United States Patent [19]

Farber

[11] Patent Number: 5,602,042

[45] Date of Patent: Feb. 11, 1997

[54] METHOD AND APPARATUS FOR MAGNETICALLY SEPARATING BIOLOGICAL PARTICLES FROM A MIXTURE

[75] Inventor: Fredric Farber, Brookline, Mass.

[73] Assignee: Cytyc Corporation, Boxborough, Mass.

[21] Appl. No.: 227,665

[22] Filed: Apr. 14, 1994

[51] Int. Cl.[6] ................................................. G01N 33/553
[52] U.S. Cl. ........................ 436/526; 209/214; 209/222; 210/695; 210/767; 435/2; 435/4; 435/7.1; 435/7.2; 435/7.21; 435/7.23; 436/501; 436/518; 436/807; 436/824
[58] Field of Search ............................... 209/214, 217, 209/222, 223.1, 225, 226; 210/695, 222, 767; 435/2, 4, 5, 7.1, 7.2, 7.21, 7.23, 7.31, 7.32; 436/174, 177, 501, 518, 526, 807, 824

[56] References Cited

U.S. PATENT DOCUMENTS

| | | | |
|---|---|---|---|
| 4,677,055 | 6/1987 | Dodin et al. | 435/7.32 |
| 5,143,627 | 9/1992 | Lapidus et al. | 422/58 |
| 5,212,085 | 5/1993 | Wands et al. | 435/240.27 |
| 5,215,926 | 6/1993 | Etchells, III et al. | 436/501 |
| 5,240,856 | 8/1993 | Goffe et al. | 435/299 |
| 5,340,749 | 8/1994 | Fujiwara et al. | 436/526 |

OTHER PUBLICATIONS

Miltenyi et al, "High Gradient Magnetic Cell Separation With MACS[1]," Cytometry, pp. 231–238 (1990).
Kemshead et al., "Magnetic Separation Techniques: Their Application To Medicine," Molecular and Cellular Biochemistry, vol. 67, pp. 11–18 (1985).
Gaudernack et al., "Isolation Of Pure Functionally Active CD8[+]T Cells," Journal Of Immunological Methods, vol. 90, pp. 179–187 (1986).
Treleaven et al., "Removal Of Neuroblastoma Cells From Bone Marrow With Monoclonal Antibodies Conjugated To Magnetic Microspheres," The Lancet, pp. 70–73 (1984).
Iyengar et al., "Human Stools As A Source Of Viable Colonic Epithelial Cells," Methodology, vol. 5, pp. 2856–2859 (1991).
Albaugh et al., "Isolation Of Expoliated Colonic Epithelial Cells, A Novel, Non–Invasive Approach To The Study Of Cellular Markers," International Journal of Cancer, vol. 52, pp. 347–350 (1992).

Primary Examiner—Paula K. Hutzell
Assistant Examiner—Susan C. Wolski
Attorney, Agent, or Firm—Lahive & Cockfield

[57] ABSTRACT

An apparatus and method provide automated collection and transfer of particles from a liquid suspension to a glass slide for visual examination. A magnet is positioned adjacent to a solution which contains particles tagged with magnetic beads, for example cells, so that the magnetic particles flow toward the magnet and collect against a collection surface positioned between the particles and the magnet. A transfer mechanism applies a selected pressure to a second side of the collection surface for transferring collected cells to a viewing slide. The apparatus includes a device for dispersing the liquid suspension of particles prior to the collection process and for collecting particles against the collection surface with a spatial distribution advantageous for visual examination. The transfer operation maintains this spatial distribution. The cell-dispersing device and the collection surface are on a common structure, for unitary movement, and which is readily disposable and replaceable for each sample of particles

31 Claims, 4 Drawing Sheets

METHOD AND APPARATUS FOR MAGNETICALLY SEPARATING BIOLOGICAL PARTICLES FROM A MIXTURE

FIELD OF THE INVENTION

The field of the present invention relates to apparatus and methods for isolating materials out of a mixture and more particularly, to apparatus and methods that couple magnetic beads to particles for magnetically separating the particles out of the mixture in a controlled manner. The invention has application, for example, as an automated device for separating biological particles from a mixture in a facile process, and for transferring the particles to a microscope slide as a thin, even layer amenable to optical analysis.

BACKGROUND OF THE INVENTION

Many common substances, such as blood, soil and tap water, are actually mixtures of different materials combined in varying proportions. For example, a blood sample is a complex mixture of proteins, cells and other materials combined in different proportions and in different concentrations throughout the volume of the sample. Often a major task during the analysis of these substances is separating the components out of the mixture so that they can be studied in isolation.

One known technique for separating the components of a mixture binds magnetic beads to the particles of interest and draws the particles of interest out of the mixture through the application of a magnetic field. Typically these magnetic assays include paramagnetic beads and an agent that binds with particles of the desired component group. The agent is selected for its specificity to the particle of interest. For example, to select the positively charged particles dispersed in a mixture, a negatively charged agent can be selected. In another example, binding agents can be selected that have antigen specificity for a protein particle in the mixture. Commonly, the agent is bound to the surface of the magnetic bead so that when the agent reacts with selected particles it binds the paramagnetic bead to the particle. The particles bound to the paramagnetic beads can be isolated out of the mixture by applying a magnetic field to the mixture to remove the bead, and the bound particle, from the mixture.

In one particular magnetic separation assay, the MACS Cell Sorter, *High Gradient Magnetic Cell Separation with MACS*, Miltenyi et al., Ctyometry 11:23 1–238 (1990), a magnetic filter is formed that collects cells bound to superparamagnetic particles. The cells are contained in a fluid mixture placed in a sterile container. Magnetic beads are coated with cell-specific antigen and dispersed into the mixture to react with the cells of interest. The beads that bind to a cell effectively imbue that cell with a magnetic moment.

In practice, an operator pours the cell-containing fluid mixture through the MACS magnetic filter that collects the cells bound to the magnetic particles. The filter is formed as a titration column seated between the poles of a permanent magnet. Located within the column is a ferromagnetic steel wool mesh of select porosity. The magnet magnetizes the steel wool and as the fluid mixture flows through the steel wool, the cells bound to magnetic particles collect against the steel wool. Once the mixture has passed through the filter, the column is unseated from the magnet and the steel wool demagnetizes. The collected cells within the steel wool are eluted by a strong wash passing through the column and dislodging the cells from the steel wool mesh.

The cells collect in the wash fluid to form a target rich fluid suspension. In a subsequent step, the cells in the fluid are analyzed using flow cytometry and statistical data regarding the target cell population is collected.

Although magnetic filtering offers a general assay for magnetically collecting particles from a fluid mixture, it still suffers from the disadvantages generally associated with the filtering process. In particular, the filtering technique is a time-consuming and laborious process that typically requires multiple repetitions of the filtering step in order to sufficiently isolate the particles from the mixture. Therefore, the filtering technique is not a particularly efficient method for isolating rare particle sub-populations.

Furthermore, the filtering technique is fairly non-specific in that it collects the magnetic particles along with particles that are sized to be captured in the steel wool mesh. As such, the magnetic filtering technique is poorly suited for extracting a pure subset of the target cell population. Similarly, the filtering technique is fairly limited to fluid samples that are sufficiently fluid to flow through the steel wool mesh and is difficult to use with more viscous samples.

In addition to being non-specific, the magnetic filter technique is nonquantitative and provides limited control over the number of target particles collected from the fluid mixture. As such, the magnetic filtering technique is poorly suited for extracting a specific quantity of target particles.

Furthermore, the filtering technique relies on a washing procedure that removes the particles from the filter and collects the particles into a wash fluid. During this procedure the wash fluid is typically contaminated by the steel-wool filter mesh. Therefore, before analysis of the isolated particles can begin, a subsequent step is necessary to separate the particles out of the contaminated wash fluid. As such, the magnetic filtering technique fails to provide a one-step system that can isolate target particles from a mixture and yield particles in a form suitable for immediate laboratory analysis.

In view of the foregoing, an object of the present invention is to provide methods and systems for extracting a specific particle sub-population from a mixture, and more particularly, to provide improved methods and apparatus for magnetically extracting particles from a mixture.

A further object of the present invention is to provide a magnetic separation system that detects the collection of target particles against a collection surface and that is further capable of indicating the number of target particles being collected from a mixture.

Still another object of the present invention is to provide a mechanism for extracting target particles from a mixture in a manner that achieves a select spatial distribution suitable for transfer to an optical element.

Yet another object of the invention is to provide improved methods and apparatus for extracting cells from a mixture that is facile to use and has a reduced number of steps.

Yet a further object of the invention is to provide an improved method and apparatus for magnetically extracting a target cell population from a mixture in a manner that reduces the number of vessels contaminated by the mixture.

These and other objects of the invention are evident in the figures and description that follow.

SUMMARY OF THE INVENTION

The invention achieves the aforementioned objectives by providing, in one aspect, a device that magnetically collects from a fluid sample the biological particles that are coupled to magnetically activatable tag elements. The device collects these particles by having a magnet element that generates a flow of tagged particles within the fluid mixture, and by having a plate element with a surface that is placed into the fluid sample and positioned within the flow of tagged particles. The device removes the collected particles from the fluid sample by having a transfer system, coupled to the plate, that withdraws the plate out of the fluid so that the particles collected thereon are isolated from the fluid sample.

The term biological particles is used herein to encompass cells, mycoplasma, viruses and particles in general that can be bound by antibodies. Cells, as the term is used herein, includes biological cells of any origin, including prokaryotic and eukaryotic organisms.

A fluid sample, as the term is used herein, encompasses substantially liquid sample material, such as sera, urine or tap water. The term fluid sample can further encompass a more dense fluid material such as a diluted slurry of feces or bone marrow.

A device for removing tagged biological particles from a fluid sample, as described above, has application as an isolation technique to facilitate study and disease therapy. For example, a magnetic cell separation technique according to the present invention can be applied to a heterogeneous fluid suspension of various cells, proteins, viruses and other particles, both biological and non-biological. In this example, the tag elements can be beads having an exterior coating of ligands with specific affinity to molecules or structures on or within the cell membrane of a target cell population. The beads can be formed from a superparamagnetic material. Upon exposure to a magnetic field the superparamagnetic material becomes polarized and the cells bound to the beads flow through the fluid toward the magnetic field source. The plate is positioned within the magnetically induced flow of bead bound cells, so that cells collect against the plate surface. The cells are held against the surface by the force of the magnetic field, as well as by any mechanical adherence that results from the cells contacting the plate surface. Since the cells are now held against the plate surface, the cells can be isolated out of the fluid sample by the transfer element that withdraws the plate from the fluid.

The provision of both the plate with a collection surface, and a transfer element that can remove the plate along with the collected cells thereon, attains superior performance. Particularly, a device in accord with the present invention can extract magnetically tagged cells directly from a fluid medium, without using a wash fluid. Therefore, the present system reduces the number of required steps and limits the production of biologically contaminated waste fluid and containers. Additionally, a device in accord with the invention has a construction that collects a layer of cells against a removable plate. Further, the connection of the plate to the transfer element allows the cells to be isolated from the fluid sample while maintaining the spatial distribution of a collected layer of cells.

A further feature of the invention is that the magnet and the plate are preferably configured to direct the flow of tagged particles to selected portions of the plate surface. For example, the magnet element can be arranged with the plate element so that the generated magnetic field is stronger at selected areas of the plate surface. The provision of a spatially varying magnetic field enables the device to control the spatial distribution of the cells collected against the plate. In a preferred embodiment, the magnet element is positioned vertically above the plate, and couples to the plate at select locations for providing a stronger magnetic attraction at these locations. Alternatively, the magnet element can be fixed at one point on the periphery of a rotating disc that is disposed vertically above the plate. The rotating disk moves the magnet element relative to the plate to spatially vary the magnetic field. This configuration achieves a more uniform spatial distribution of the particles collected against the surface. Other configurations for spatially varying the magnetic field can use a distributed array of magnet elements that can be selectively activated and deactivated.

A further feature of the invention is that the plate can connect to a vessel housing that, in one embodiment, can be formed as a cylindrical tube open at both ends, with the plate attached at one end to span the tube opening. In a preferred embodiment, the plate is non-permeable to the fluid sample and is sealed fluid-wise to the tube opening to form an interior chamber that can receive the magnet element, and fluidicly seal the magnet element from the fluid sample when the plate surface and the vessels are disposed into the fluid sample. As such, each vessel and plate assembly can form a disposable housing that fits over the magnet element so that the magnet element is positioned proximate to the plate, and within the fluidicly sealed chamber. Each vessel and plate assembly can be used for a single sample, while the magnet element can be used repeatedly. The invention thus provides an exceedingly hygienic and cost effective structure.

A further advantage of this configuration is that it limits the contamination of materials during the particle collection process. In particular, it limits contamination to the container holding the fluid sample and the vessel and the plate assembly. As such, the invention eliminates the containers and fluids which are contaminated during a filter wash step.

Still another feature of the invention is that the vessel housing can have fins imprinted into the sides of the housing and the housing can connect to a rotatable fixture so that the fins can be rotated within the fluid sample to generate shear forces that separate colloids, cellular tissue and other aggregates of the component parts of the fluid sample. An advantage of this structure is that it further reduces biological contamination by providing a single housing for processing a fluid sample and for collecting out of that fluid sample a specific subpopulation of cells.

In a preferred embodiment of the present invention the device collects biological particles tagged with superparamagnetic microbeads. Permanent magnets of earth metals such as samarium cobalt can be used for such procedures. Choice of the magnetic system is dependent on the particles used to target the particular cell sub-population. The microbeads have antibodies immobilized on the exterior bead surface. The specificity of the immobilized antibodies can be directed to a protein or to an antigen of a cell sub-population being extracted from the mixture. The microbeads can be much smaller than the targeted cells, typically 1 μm in diameter, as compared to a 50 μm cell diameter. The use of superparamagnetic beads provides particles tagged with beads that are non-magnetic unless in the presence of a magnetic field, and therefore do not aggregate to form magnetically bound colloids. Upon binding to the target cell surface or upon being absorbed through the cell membrane and into the cell, the beads give the selected biological particles an activatable magnetic property.

A preferred, but optional step, removes the beads bound to the surface of the target particles. This step enhances the optical analysis of the collected particles by reducing the number of beads that conceal portions of the particles during analysis. In one optional procedure, the particles on the plate element are washed with a fluid that dislodges the beads bound to the particles and elutes the beads into the fluid. The fluid is antigen rich to compete the bead anti-bodies off the particles. Alternatively, the fluid can contain a protease agent to cleave the anti-body from the micro particles. Other fluids and techniques generally known in the art can be used to remove the beads.

An antibody, as the term is used herein, may include any of the family of structurally related glyco-proteins produced by B lymphocytes and that operate as part of specific humoral immunity, and that include an antigen combining site. An antigen, as the term is used herein, can include any substance that may be specifically bound by an antibody molecule.

Superparamagnetic, as the term is used herein, can describe a magnetic behavior that includes a selectable magnetic state activated by a magnetic field and deactivated upon removal of the magnetic field.

A further feature of the present invention is that the transfer element transfers the particles collected against the plate surface to a receiver, such as a microscope slide, for further analysis. In particular, the transfer element contacts the particles collected against the plate surface against the receiver so that the particles transfer to the receiver. Further, the transferred particles have the same spatial distribution as they had on the plate surface prior to transfer. One preferred distribution in a substantially uniform monolayer. In a further embodiment, the transfer element can include a magnet positioned so that the receiver is disposed between the plate and the magnet. The magnet enables the magnetic transfer of tagged particles off the plate surface and onto the receiver.

In a further feature of the present invention the plate can include a diaphragm that deflects when particles collect against the surface. The deflection of the diaphragm can be measured by strain gauge elements connected to the diaphragm surface. In this way the present invention provides structure that can generate a signal representative of the collection of particles against the plate surface. The invention thus provides a new structure that enables the particle collecting device to indicate when particles have been separated out of a fluid sample.

A further feature of the invention calibrates the generated signal to provide a quantitative count of the collected particles. In one example, the amplitude of the generated signal varies in proportion to the number of magnetic beads being magnetically held against the diaphragm. The signal amplitude is compared against a table of empirically collected data relevant to that type of microbead. The data table contains information that relates the measured amplitude to the quantity of cells collected against the surface. The invention thus provides a system that has a quantitative measure of the number of particles collected, and a quantitative feedback signal that can be monitored during a collection procedure to control the quality of particles collected from the sample.

Another aspect of the present invention provides methods for separating out a specific subpopulation of biological particles from a fluid sample. These methods can include steps for providing magnetically activatable tag elements that selectively bind to a specific particle subpopulation of the fluid sample. In a further step, a magnetic field is applied to the fluid sample so that the tag elements are magnetically activated, to thereby establish a flow of tagged particles within the fluid sample. In a further step, a plate disposed within the flow of tagged particles has a surface for collecting the particles. In an additional step the plate is withdrawn from the fluid sample and the collected particles are transferred to a receiver, such as a microscope slide, for further analysis.

These and other advantages of the invention will be more clearly understood by reference to the following detailed description and attached drawings, in which like reference numbers refer to like elements.

DESCRIPTION OF ILLUSTRATED EMBODIMENTS

Figure 1:
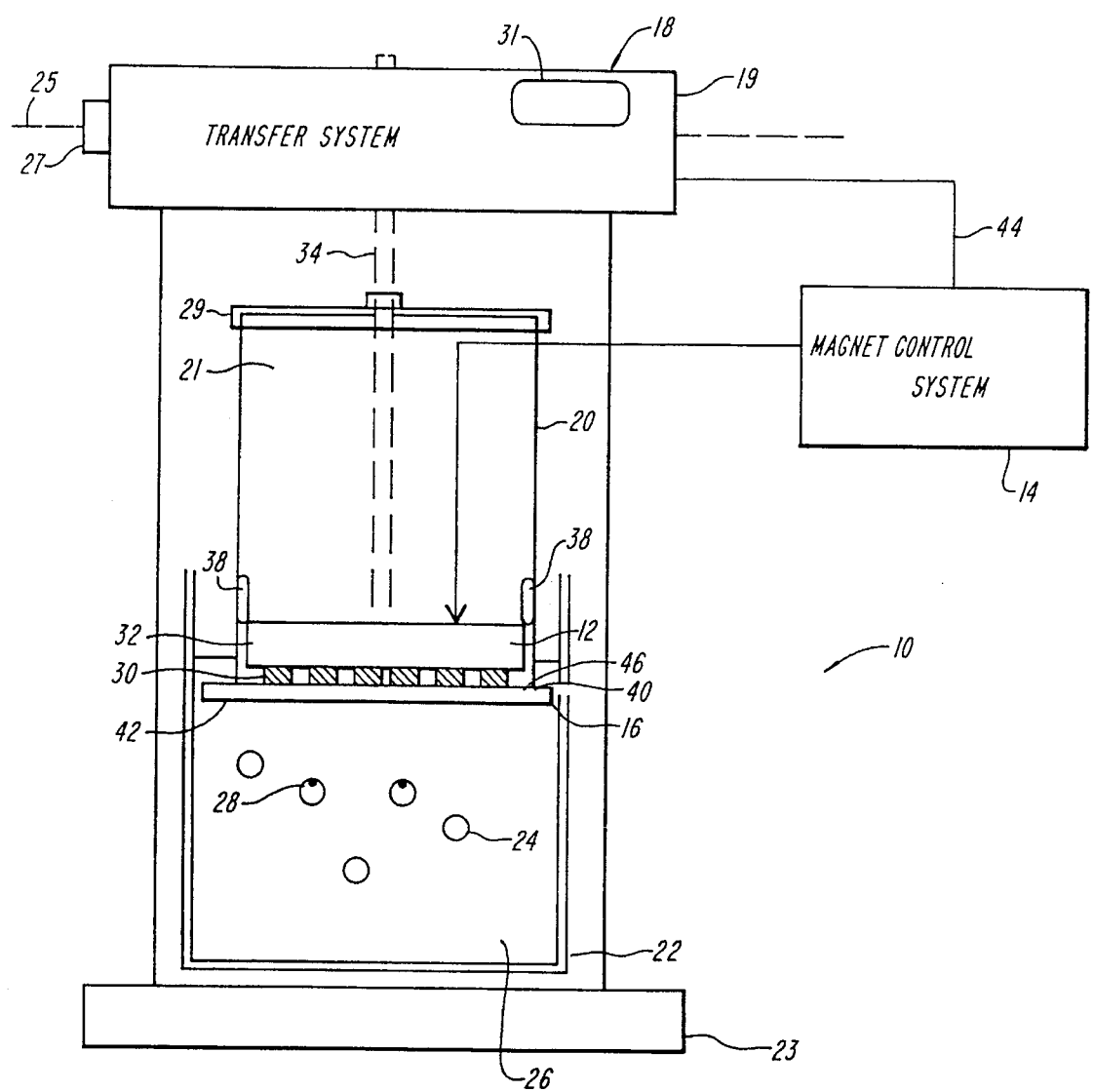
FIG. 1 is a block diagram illustration of an apparatus constructed according to the present invention for magnetically removing particles from a mixture.
Figure 2:
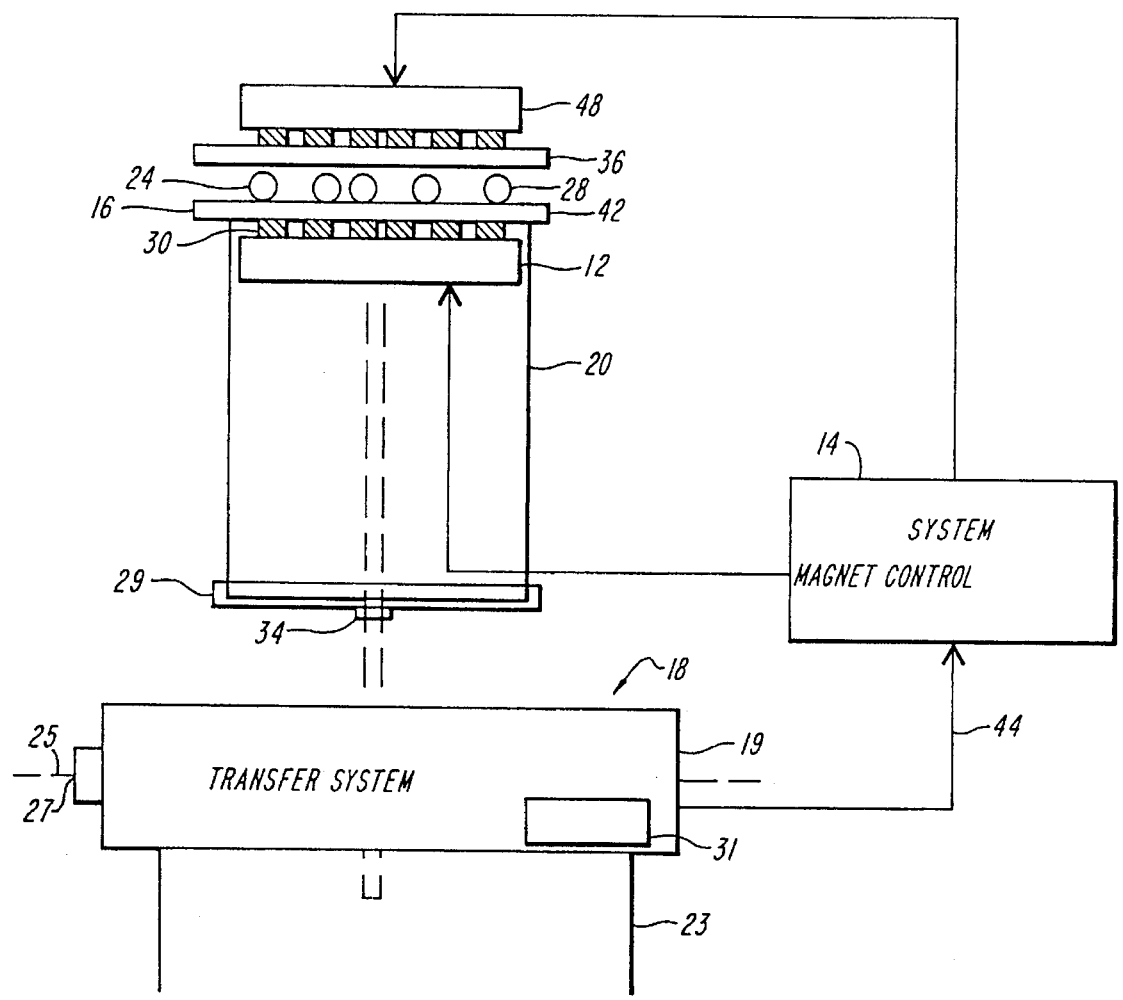
FIG. 2 is a block diagram illustration of an apparatus constructed according to the present invention for magnetically collecting particles for transfer to an optical element.

FIGS. 1 and 2 shows a system 10 according to one practice of the invention for the controlled magnetic extraction of particles dispersed within a fluid medium. The illustrated embodiment includes a magnet 12, a magnet control system 14, a plate 16, a transfer system 18 and a housing 20, connected as shown. The system 10 is configured for application to a container 22 that holds a fluid sample 26 with particles 24 dispersed throughout. As illustrated in FIG. 1 the plate 16 can be submerged by the transfer system 18 within the fluid sample so that the plate 16 is disposed into the fluid sample.

As further illustrated in FIGS. 1 and 2, the plate 16 and housing 20 form a collection vessel that is dimensioned to house the magnet 12 within the interior chamber 21. In the illustrated embodiment the vessel 20 is a cylindrical tubular body with openings at either axial end and with the plate 16 spanning and closing the lower axial end. In an optional embodiment of the invention, the vessel walls 20 include fins 38 located on the exterior surface of the vessel walls. The fins 38 form recessed surfaces in the walls 20 that generate shear forces in the fluid sample 26 upon rotation of the vessel 20. The plate 16 is preferably formed from a non-porous material, such as aluminum, polystyrene, polyethylene or conventional plastic and is sealed to the lower end of the vessel walls 20 to form an interior chamber 21 that can isolate the magnet 12 from contact with the fluid sample 26 when the collection vessel is extended into the container 22.

In the illustrated embodiment, the plate 16 is positioned between the fluid sample 26 and the magnet 12. The plate 16 is a thin disc that has a first surface 46 with a peripheral portion 40 that connects to the vessel walls 20 and a second surface 42 that faces outward from the vessel. The plate 16 is preferably non-porous to the fluid sample 26 and sealed fluid-wise along the peripheral portion 40 to the housing 20 to isolate the magnet 12 fluidwise from the fluid sample 26. The plate surface 42 is preferably a substantially planar, non-magnetic surface that forms a collection surface for the target particles in the fluid sample 26.

The plate 16 is preferably formed from a non-magnetic material or a non-ferro-magnetic material so that the strength of the magnetic field generated by the magnet 12 is not affected by a magnetic moment generated by the plate 16. In a preferred embodiment of the invention, the plate 16 has a smooth planar surface 42 for collecting particles thereon. The diameter of the surface 42 is preferably large enough to span the entire width of the magnet 12. In this way, the surface 42 defines a plane that extends transversely through the magnetic field generated by the magnet 12. In this way, the collection surface 42 is positioned into the path of magnetic particles flowing toward the magnet 12. As illustrated in FIG. 1, the plate 16 can span substantially the entire width of the container 22 to effectively prevent cells 24 from collecting against the walls 20 of the housing when the magnet 12 is activated.

As further depicted in FIGS. 1 and 2, the magnet 12 can sit against the plate 16 within the housing 20. In the illustrated embodiment, the magnet 12 is a magnetic system that includes the magnetic posts 30 extending between the magnetic body 32 and the upper surface 46 of the plate 16. The posts 30 are arranged against the surface 46 to produce a magnetic field with a selected spatial distribution. The posts 30 can be arranged against the surface of the plate 16 to vary the strength of the magnetic field generated by magnet 12 across the collection surface 42. The magnet 12 is selected to generate a strong magnetic field capable for exerting a magnetic moment on the magnetic micro-particles 28 bound to cells 24 and dispersed throughout the entire volume of fluid sample 26. In the illustrated embodiment of FIG. 1, the magnet 12 is an electro-magnet operated under the control of the magnetic control system 14. The posts 30 that extend between the body 32 of magnet 12 and the plate 16 can be individual electro-magnets operated under the control of system 14. The posts 30 under the control of system 14 form a spatially distributed array of magnetic elements that allows the strength of the magnetic field to be varied over the area of the surface 42. In a preferred embodiment, each post 30 is separately activatable by the control system 14. Further, the control system 14 preferably controls the strength of the magnetic field generated by each post 30 to provide a magnetic system 12 that is time-varying and spatially varying under the control of the control system 14. In an alternative embodiment of the invention, the magnet 12 can be a rare earth permanent magnet including cobalt-iron, nickel-iron, or samarium-cobalt.

The transfer system 18 illustrated in FIGS. 1 and 2, has a control unit 31 that controls the mechanical arm 34 that extends from the transfer system 18 through the housing 20 and connects to the magnet 12. The transfer system 18 is configured to lift the housing 20, magnet 12 and plate 16 out of the fluid sample 26 while maintaining the magnetic field generated by magnet 12. The mechanical linkage arm 34 can be operated by the transfer system 18 to extract the housing 20, magnet 12 and plate 16 from contact with the fluid sample 26. In a preferred embodiment of the invention, the housing 20 and plate 16 form a collection assembly that can removably and replaceably connect into the system 18 and fit around the magnet 12 to fluidically isolate the magnet 12 from the fluid sample 26. In the illustrated embodiment, the collection assembly fits into and frictionally engages with the cap 29 that connects to the mechanical arm 34. The collection assembly moves with the mechanical arm 34 as the magnet 12 is extended toward and extracted away from the fluid sample 26 by the transfer system 18.

The illustrated transfer system 18 includes a transport mechanism 19 and a base 23. The transport mechanism 19 includes the electric motor 27 and the gear assembly, not shown, that connects to the mechanical linkage arm 34 that connects to the magnet 12. The illustrated transfer system 18 can selectively position the removable and replaceable housing 20 and plate 16 collection assembly. The transport system 19 provides both vertical movement, by lowering and raising the mechanical arm 34, and horizontal movement, by pivoting the mechanical arm 34 about the axis 25, to collect particles on to the plate 16 and to position the plate 16 for transferring the collected particles to a receiver element.

Additionally, the illustrated transfer system 18 provides rotational movement, through the motor 27 and the gear assembly, of the collection assembly, to rotate the collection assembly about the mechanical arm 34 to act in concert with the fins 38 to provide shear forces to the fluid sample 26. The transfer system 18 selectively applies the shear forces to fluid sample 26 that disperse cells in the sample fluid. The transfer system 18 and collection assembly thus has one function as a dispersing rotor, for separating sample cells suspended in the fluid sample.

The illustrated transport mechanism 19 connects to the mechanical arm 34 through the gear assembly, not shown, that operates in concert with the electric motor 27 to drive the arm 34 relative to the axis defined by the arm 34. The electric motor 27, secured to the transfer system 18 and connected to the gear assembly, drives the mechanical arm 34 in either direction, toward and away from the transfer system 18. The gear assembly can include a worm gear assembly or other gear assembly known in the art of mechanical systems, for linearly actuating a rod responsive to a rotational motion.

The transfer system 18 of the illustrated system 10, which mounts and positions and drives the collection assembly for the forgoing cell-dispersing and sample-collecting functions, also functions to transfer collected cells to a receiver element 36, preferably a viewing slide.

In the illustrated embodiment, the transport mechanism 19, pivots relative to axis 25 and positions the plate 16 for cell transfer. The transport mechanism 19 couples to the mechanical arm 34, and pivots the arm 34, relative to axis 25, when the transfer system 18 extracts the collection assembly from the container 22. In one embodiment, the pivoting action is controlled by the motor 27 and the gear assembly. The pivot angle is selectable through the 180° defined by the arm 34 in the low position when directed into the container 22, and the arm 34 in the high position, when positioned above the illustrated transfer system 18 and with the plate 16 directed away from the transfer system 18.

With reference to FIGS. 1 and 2, the transfer system 18 can be seen to have a transfer magnet 48 and a receiver element 36, such as a slide. The transfer system 18 is depicted in FIG. 2 with the mechanical arm 34 in the high position. The collection assembly is extracted from the fluid sample 26 and pivoted into the high position by the motor 27. The plate 16, with the collected particles 24, faces the optical element 36. The optical element 36 couples to the transfer magnet 48, and the magnet 48 is in electrical circuit with the magnet control system 14. The magnet control system 14 is in electrical circuit with the magnet 12. In the depicted embodiment, the magnet 12 and the magnet 48 are electro-magnets operated under the control of system 14.

The system 14 is in electrical circuit with the transfer system 18 via the signal transmission line 44. The transfer system 18 transmits, via transmission line 44, a position signal representing the present position of the plate 16. Responsive to the position signal, the magnet control system 14 deactivates the magnet 12 and activates the transfer magnet 48. Typically, the transfer system 18 transfers the particles in response to a position signal indicating that the arm 34 is in the high position and thus adjacent to the receiver 36. As will be explained in greater detail hereinafter, the illustrated transfer magnet 48 magnetically collects the cells 24 onto the surface of the slide 36 with a substantially identical spatial distribution as on the plate surface 42.

A preferred spatial distribution of cells is a thin even monolayer of cells distributed on the surface of the receiver element 36. This transfer can be accomplished by activating the transfer magnet 48, by pressing the surface 42 against the surface of the receiver 36 or by a combination of pressing and magnetic action performed under the control of the control unit 31 within the transfer system 18 and the magnet control system 14. The control unit 31 is typically a programmable control unit of the type adapted for monitoring and generating analog signals and for digitally processing these signals according to a stored instruction program. In one embodiment, the control 31 unit can be a conventional PC computer system with an Analog to Digital interface card. However, other control units, including integrated data processing hardware or mechanical relay systems could be substituted without departing from the scope of the present invention.

The fluid sample 26 can be a liquid sample of a biological material, such as sera, that contains a variety of components including cells, proteins, minerals and a variety of other substances. In the illustrated embodiment, the particles 24 can be cells, proteins or other biological material. A sub-population of the particles 24 can be tagged with magnetic beads 28 that can bind to the exterior of the biological particles 24. In a preferred embodiment, the beads 28 are micro-particles formed from superparamagnetic crystals that have antibodies bound on the surface of the bead. These superparamagnetic micro-particles are added into the fluid sample 26 and dispersed throughout so that the antibodies bound on the surface of the micro-particles can react with and bind to a specific sub-population of cells 24 dispersed within the fluid sample 26. The cells 24 that bind to the micro-particles 28 are thus tagged with a magnetically activatable bead that imbues to the cells 24 with a magnetically selectable magnetic moment.

The microbeads 28 can be any magnetically responsive particle having an exterior surface coated with a layer of material suitable for absorbing one or more biological protein molecules, such as antigens or antibodies, and that are suitable for binding to or being absorbed into biological materials, such as cells or viruses. Various types of such microbeads are commercially available either as completed beads or as kits for forming such beads.

The selection of microbead is generally determined by the application, and particularly the size and quantity of particles being collected from the fluid sample. Typically, the bead has a metal oxide core or cores and is coated with a layer of polymer. Preferably, the core is either superparamagnetic or paramagnetic although ferromagnetic cores may also be used, particularly if a centrifugation step is employed during separation. The selected bead can act as a tag for the target particle by binding particle specific agents to the bead exterior. In a preferred embodiment, the beads can be tags for biological particles by binding anti-bodies to the exterior surface of the bead. Typically, the antibodies are fixed to the beads by chemical coupling or by adsorption. In alternative embodiments, the tags can be specific for non-biological particles, by binding agents specific to non-biological characteristics of the target particle. In one example, positively charged ions can be bound to the particle surface for tagging the negatively charged particles within the fluid sample. Other such variations can be practiced without departing from the scope of the present invention.

The microbeads can disperse throughout a cell mixture. The cell mixture is typically a heterogeneous slurry of mostly unknown cells that includes in the mix a sub-population of the target cells. The target cells are often a small portion of the overall cell mixture that is dispersed throughout the slurry. The slurry is typically a fluid mix that can be contained in a sterile, disposable container, such as container 22. The slurry and microbead mixture can incubate in the container for short time at a low temperature while being gently agitated. This incubation allows the antibodies to attach to the target cells and to form strong molecular bonds that join the beads to the cells. Agitation can be applied by the transfer system 18 rotating the collection assembly to gently stir the fluid sample 26.

The cells that bind to microbeads can be isolated from the general mix by the magnetic field of magnet 12 that draws the dispersed cells to the collection surface 42. As depicted in FIG. 2, the magnet 12 connects to a mechanical linkage 34 for drawing the magnet out of the slurry and for placing the flat non-magnetic surface 42 against the surface of a receiver element 36, such as a microscope slide. The magnet 12 releases the cells to the slide by deactivating the magnetic field and thereby deactivating the magnetic property of the superparamagnetic microbeads. In the embodiment depicted in FIG. 2, the cells are transferred onto the microscope slide by a magnet 48 positioned behind the slide 36 to draw the cells off the collection surface 42 and onto the slide surface. It is herein noted that some dimensions in FIG. 2 have been exaggerated for emphasis and for clarity.

The cells collected on the microscope slides 36 can be stained and examined for morphological evidence of cancer or for other cytological conditions. The microbeads incorporated into the cell membrane are orders of magnitude smaller than the cell under examination and therefore minimally interfere with light microscopy.

In an optional step, the microbeads 28 bound to the cell surface are removed before optical analysis. This is a preferred optional step if the selected micro-particles are relatively large compared to the target biological particles, or if a binding agent is selected that will bind particles to many locations on the particle surface. In the optional step, the particles collected on the plate surface 46 are washed with a solvent fluid that removes the beads from the particles 24. In one example, the particles are washed with a competing fluid that is rich with anti-body compatible material, for competing the micro-beads off the particles. Alternatively, the beads 28 are removed by washing the particles in a protease containing fluid that cleaves the anti-body from the bead 28. This step can be administered by extracting the collection assembly from the container 22 and replacing the container 22 with a second container having the selected wash fluid. The transfer system 18 can extend the collection assembly into the wash fluid and gently rotate the plate 16 relative to the wash fluid. Additionally a second fluid container can hold a transfer fluid that facilitates the transfer of particles from the plate 16 to the slide 36.

With reference to FIG. 1 and FIG. 2, at the start of the operation of the system 10 for extracting particles coupled to magnetic beads, the fluid container 22 is filled with a fluid sample 26 having particles 24 contained therein. Typically the container 22 is a sterile container for storing a biological fluid sample such as blood in a cup shaped container that is opened at the top. The micro-particles 28 are dispersed within the fluid sample 26 and mixed with the sample to allow the particles 28 to disperse throughout the volume of the sample 26 and to react and to bind with the particles 24 of the target subpopulation. Once the particles 28 have been given sufficient time to react to the target sub-population of particles 24, the transfer system 18 lowers the plate 16 into fluid communication with the fluid sample 26. Once the plate 16 establishes fluid communication with the fluid sample 26 the magnet control system 14 activates the magnet 12 to generate a magnetic field that radiates through the fluid sample 26. The super paramagnetic property of the beads 28 is affected by the magnetic field so that the beads become magnetic materials. As such the magnetic beads 28 bound to the sub-population of target particles 24 are effectively drawn to the magnet 12 and a magnetic flow of particles is established within fluid sample 26.

As illustrated in FIG. 1, the plate 16 is disposed between the magnet 12 and the particles 24 with a geometry such that particles drawing toward the magnet 12 collect on the surface of the plate 16 and magnetically adhere to it. In one preferred practice, the magnet posts 30 are selectively activatable by the control system 14. The magnet control system 14, selectively activates the posts 30 and thus generates a spatially-varying and time-varying magnetic field. The resultant varying magnetic field causes the magnetically-induced movement of the particles and the particles 28 are distributed across the surface of plate 16 by the selectively activated posts 30. In this way, a specific spatial distribution of particles 24 is collected against a plate 16. After a selected collection time, the transfer system 18 withdraws the plate 16 from fluid communication with the fluid sample 26, extracting from the fluid sample 26 the cells collected against plate 16 and magnetically adhering thereto.

With reference to FIG. 2, in the operation of transfer system 18, the plate 16 is disposed proximate to a receiver element 36, such as a slide lens. The receiver element 36 is positioned between the plate 16 and the transfer magnet 48. The transfer system 18 generates a signal carried via transmission line 44 to signal the magnetic control system 14 to deactivate the magnet 12. The superparamagnetic beads are readily demagnetized once the magnetic field generated by the magnet 12 is removed. In the depicted embodiment, the particles adhering to the plate 16 are collected against the receiver 36 by the transfer system 18 activating the transfer magnet 48. By positioning the plate 16 proximate to the receiver 36, the particles collected on the plate 16 can be transferred with substantially the same spatial distribution as collected against the surface 42 of the plate 16. The transfer magnet 48 draws the particles to the surface 36 and magnetically adheres the particles thereto. In a preferred embodiment of the invention, the transfer magnet 48 is an electromagnet controlled by the transfer system 18 to affect the transfer of particles 24 onto a microscope slide 36.

Figure 3:
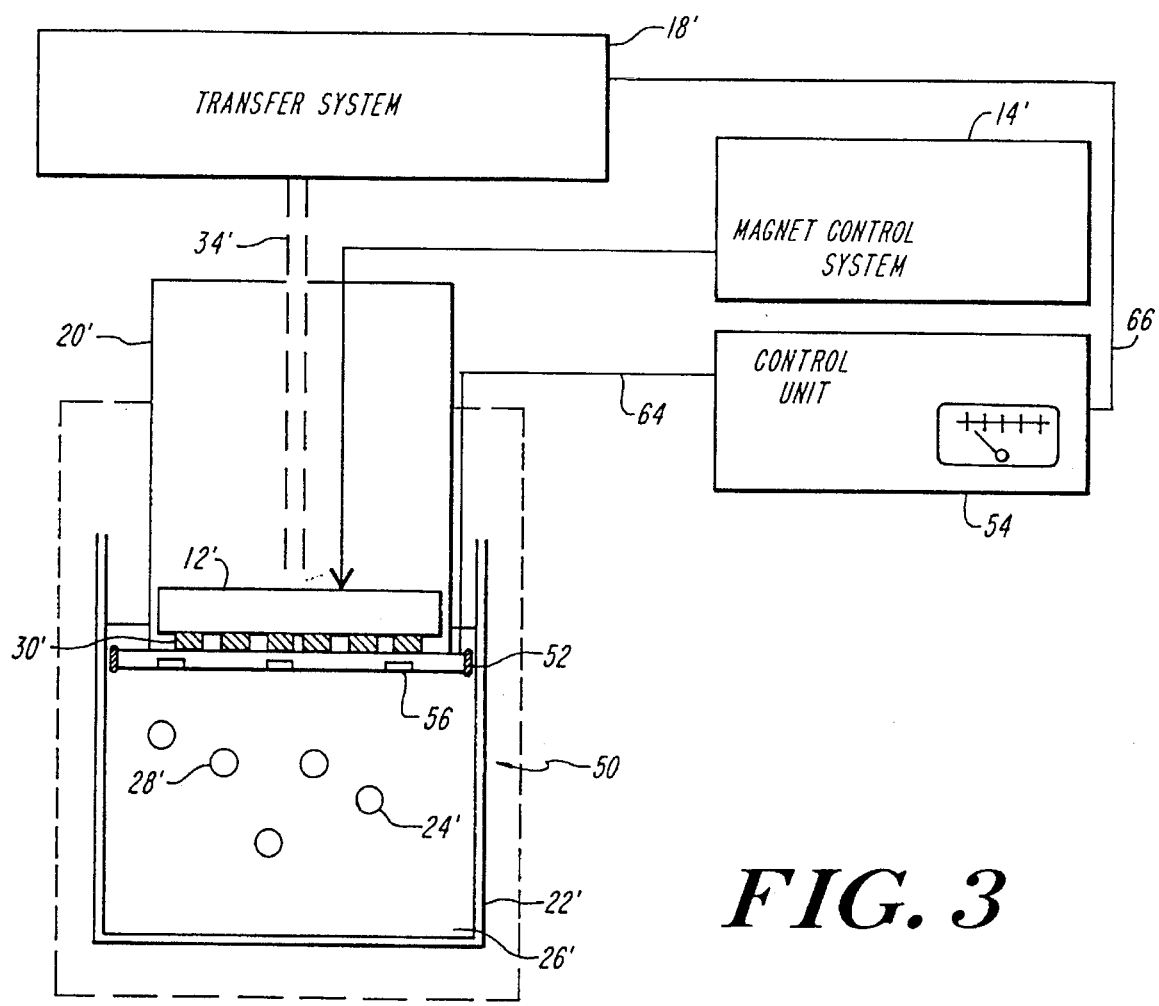
FIG. 3 is a block diagram illustration of a further embodiment of the present invention that includes a particle detection assembly.
Figure 4:
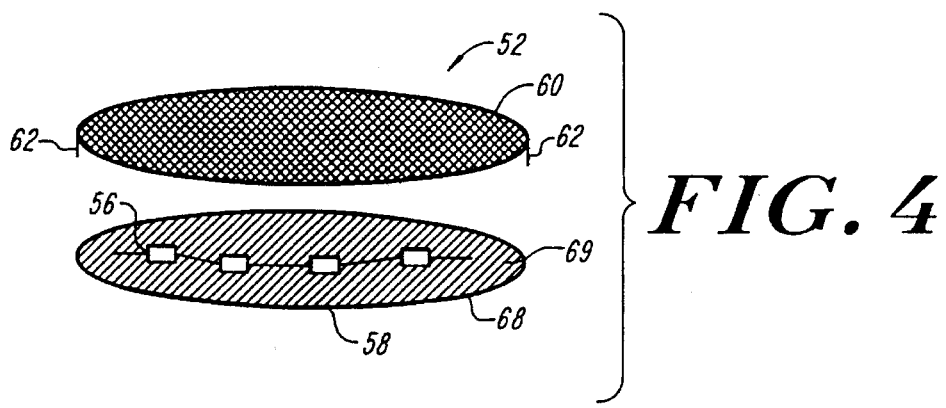
FIG. 4 illustrates in more detail a collection surface of the particle detection assembly.

FIG. 3 and FIG. 4 show a second embodiment of the present invention in which a system 50 for magnetically extracting a select quantity of particles 24' from a fluid sample 26' includes a transfer system 18' and a magnet control system 14', a magnet 12', a plate assembly 52 and a control unit 54. In the depicted embodiment, the plate assembly 52 is in electrical circuit with the magnet control unit 14' via transmission line 64. Elements 20', 22', 28', 30' and 34' refer to like-numbered elements 20, 22, 28, 30 and 34 discussed previously in the context of FIG. 1 and 2.

The exploded view of FIG. 4 shows that the plate assembly 52 includes a lower plate 58, an upper plate 60, seal members 62 and strain gauges 56. The strain gauges 56 as depicted in FIG. 4 are disposed along the upper surface 69 of plate 58 and across the center of the plate. Seal members 62 connect upper plate 60 to lower plate 58 and form a perimeter seal between the plates 60 and 58. Preferably the perimeter seal is a fluid-tight seal that isolates the strain gauges 56 from the fluid sample 26. Lower plate 58 is preferably formed from a thin non-magnetic, non-porous material which is readily deflectable. The lower surface of plate 58 forms the collection surface 68 for collecting particles thereon.

In the illustrated embodiment, the plate 58 forms a deflecting diaphragm that deforms in response to the collection of a magnetically attached particles to magnet 12'. The plate assembly 52 connects via the transmission line 64 to the control unit 54. Control unit 54 measures the signal generated by the strain gauges 56 disposed on plate 58, to determine the relative force applied by the particles 24' collected against the surface 68 of the plate 58. It is understood that the magnetic field acting on the particles 24' deflects the plate 58 in proportion to the number of particles collected against the surface. The strain gauges 56 therefore generate a signal representative on the collection of particles 24' against the plate 58.

As particles 24' continue to collect against the plate 58 the mechanical force of the particles attracted to the magnet 12' increases. The strain gauges 56 generate a signal representative of the collection of particles 24' against the surface 58. The strain gauges thus generate a qualitative signal that indicates that particles 24' have collected against the surface 68. Optionally, the control unit 54 can include a data processing system that analyzes the signal from strain gauges 56 and determines a quantitative signal that represents the number of particles 24' collected against the surface 68. In one embodiment, the control unit 54 includes an empirically recorded table of data that correlates that quantity of particles 24' collected to the amplitude of the signal generated by the strain gauges 56. Thus, the strain gauges 56 generate a signal representative of the quantity of particles 24' collected against the plate 58. The plate assembly 52 transmits this signal via the transmission line 64 to the control unit 54. The depicted control unit 54 is in electrical circuit with the transfer system 18', via transmission line 66. The control unit 54 generates a transfer signal responsive to the force of particles against the plate 52, to activate the transfer system 18' to remove the plate assembly 52 from fluid communication with the fluid sample 26' once a selected number of particles 24' has been collected.

Figure 5:
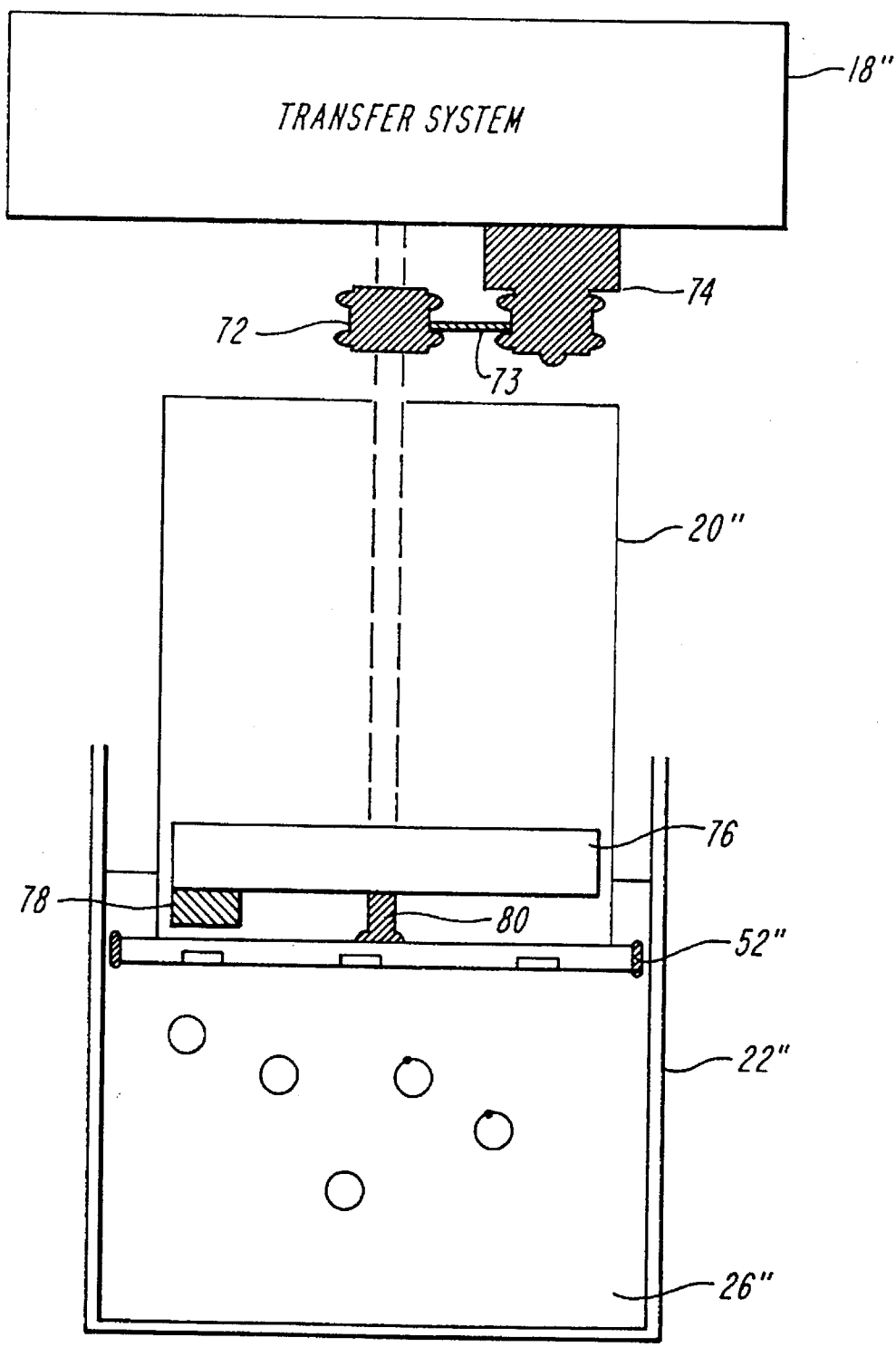
FIG. 5 is a schematic block diagram of an alternative embodiment of the invention that includes an assembly for dynamically varying the magnetic field.

FIG. 5 illustrates another embodiment of the invention that includes a linkage arm 70 that connects between the transfer system 18" and the plate assembly 52". As depicted the mechanical arm 70 includes a hub 72 connected by the belt 73 to a motor 74. At the lower axial end the mechanical arm 70 connects to a magnet 76 that has one post 78 extending from the body of magnet 76 and that includes a bearing 80 that connects between the magnet body 76 and the plate 52".

As shown in the illustrated embodiment of FIG. 5, the magnet 76 has one post 78 located at the periphery of the magnet 76. The post 78 can be rotated by spinning the magnet body 76 about the bearing 80. As a function of rotation rate, the magnetic field induced within the fluid 26 can be spatially varied. At the upper axial end of mechanical arm 70 the motor 74 operated under the control of the transfer system 18 drives the belt 73 and hub 72 to spin the mechanical arm 74 about the bearing 80. The magnet 76 selectively rotates relative to the plate 52, and spatially varies the induced magnetic field within the fluid 26" as a function of rotation rate, and therefore time. Elements 20" and refers to like-numbered elements 20 and 22 discussed previously in the context of FIG. 1 and 2.

It will thus be seen that the invention efficiently attains the objects set forth above, among those made apparent from the preceding description. It will also be understood that changes may be made in the above construction and foregoing sequences and operations without departing from the scope of the invention. It accordingly is intended that all matters shown in the accompanying drawings be interpreted as illustrative rather than in any limiting sense. It is also to be understood that the following claims are intended to cover all of the generic and specific features of the invention as described herein, and all statements of the scope of the invention which as a matter of language, might be said to fall there between.

Having described the invention, what is claimed as new and secured by letter patents is:

1. A system for collecting biological particles from a fluid medium, said system comprising tag means for dispersing in the fluid medium and comprising a magnetically responsive material having at least one substance immobilized upon an exterior surface for coupling to said biological particles, magnetic field source means for generating within said fluid medium a magnetic field to establish a flow of biological particles coupled to said tag means, plate means having a surface for positioning within said flow for collecting said biological particles thereon, and transfer means, coupled to said plate means, for withdrawal of said plate means and said biological particles collecting thereon from the fluid medium.

2. A system according to claim 1 wherein said magnetic field source means is arranged relative to said plate means to direct said flow to selected portions of said surface for collecting particles thereon.

3. A system according to claim 1 wherein said magnetic field source means includes means for directing said flow to at least one selected portion of said surface for collecting particles thereon.

4. A system according to claim 1 further comprising means for selectively moving said magnetic field source means relative to said surface for spatially distributing said particles collected thereon.

5. A system according to claim 3 wherein said magnetic field source means includes a spatially distributed array of magnetic field elements and said means for directing includes control means for controlling the magnetic field of subgroups of said elements in said array to spatially distribute said particles collected thereon.

6. A system according to claim 1 wherein said surface forms a flow barrier substantially non-permeable to said fluid medium and being substantially planar.

7. A system according to claim 1 further comprising housing means for isolating fluid-wise said magnetic field source means from said fluid medium.

8. A system according to claim 1 further comprising a tube wherein said plate means is attached to the distal end of said tube and is sealed fluid-wise to said tube to form a vessel having an interior chamber for receiving said magnetic field source means.

9. A system according to claim 8 wherein said vessel has walls for immersion into said fluid medium and for producing shear forces in said fluid medium in response to agitating movement of said vessel walls relative to said fluid medium.

10. A system according to claim 1 wherein said tag means comprises a superparamagnetic bead having at least one selected antibody bound on the exterior bead surface and having a specificity for an epitope on one or more particle subpopulations dispersed within said fluid medium.

11. A system according to claim 10 wherein said tag means comprises a selected quantity of said superparamagnetic beads.

12. A system according to claim 1 further including a transfer magnet and a receiver element, wherein said receiver element is situated between said transfer magnet and said plate means, and wherein said transfer magnet removes said biological particles coupled to said tag means from said surface of said plate means for collection of said biological particles onto said receiver element with a spatial distribution of articles substantially similar to the distribution of said particles collected on said surface of said plate means.

13. A system according to claim 1 further including a receiver element and a mechanical arm for pressing said plate means against said receiver element for transferring said collected particles to said receiver element.

14. A system for collecting a selected quantity of biological particles from a fluid medium, said system comprising tag means for dispersing in the fluid medium and comprising a magnetically responsive material having at least one substance immobilized upon an exterior surface for coupling to said biological particles, magnetic field source means for generating within said fluid medium a magnetic field to establish a flow of biological particles coupled to said tag means toward said magnetic field source, plate means having a surface positioned within said flow of biological particles for collecting said particles thereon, means for measuring a parameter responsive to the collection of particles against said surface wherein the value of said parameter changes according to the quantity of particles collected thereon, and transfer means for removing said particles collected against said surface from said fluid medium, for transfer to an optical element, in response to a selected change in the value of said measured parameter.

15. A system according to claim 14 wherein said means for measuring measures the mechanical deflection of said surface as biological particles collect thereon.

16. A system according to claim 14 wherein said measuring means includes strain gauge means mounted to said plate means for measuring the mechanical distortion of said surface.

17. A system according to claim 16 wherein said strain gauge means are resistive strain gauges mounted to said surface of said plate means.

18. A system according to claim 16 wherein said strain gauge means are capacitive strain gauges.

19. A method for collecting biological particles from a fluid medium for image analysis, comprising the steps of providing tag means comprising a magnetically responsive material having at least one substance immobilized upon an exterior surface for coupling to said biological particles, said tag means being dispersed within said fluid medium, applying a magnetic field to said fluid medium to establish a flow of biological particles coupled to said tag means, disposing plate means having a surface positioned within said flow of biological particles to collect said particles thereon, and transferring said particles from said surface to a receiver element with a spatial distribution of particles substantially similar to the distribution of said particles collected on said surface.

20. A method according to claim 19 comprising the further step of agitating said particle-containing fluid medium with a device immersed into said fluid medium for dispersing said biological particles within said fluid medium.

21. A method according to claim 19 comprising the further step of agitating said fluid medium by actuating said surface of said plate means to disperse said biological particles within said fluid medium.

22. A method according to claim 19 wherein the step of transferring said particles from said surface of said plate means to said receiver element includes the steps of contacting said surface with said receiver element and applying a pressure against said surface to transfer said particles.

23. A method according to claim 19 wherein said step of transferring said biological particles from said surface of said plate means to said receiver element includes the steps of disposing said receiver element proximate to said surface of said plate means and applying a magnetic force to said biological particles for attracting said biological particles to said receiver element, for thereby transferring said biological particles.

24. A method for collecting a selected quantity of biological particles from a fluid medium, comprising the steps of providing tag means comprising a magnetically responsive material having at least one substance immobilized upon an exterior surface for coupling to said biological particles, said tag means being dispersed within said fluid medium, applying g magnetic field to said fluid medium to establish a flow of biological particles coupled to said tag means, disposing plate means having a surface positioned within said flow of biological particles to collect said particles thereon, measuring a parameter responsive to the collection of particles against said surface, wherein the value of said parameter changes according to the quantity of particles collected thereon, withdrawing said plate means with said biological particles collected thereon from the fluid medium in response to a selected change in the value of said measured parameter, and transferring said particles collected on said surface to an optical element for image analysis.

25. A method according to claim 24 wherein said step measuring said parameter includes the step of measuring deflection of said surface as particles collect thereon.

26. A method according to claim 24 wherein said step of measuring includes the step of disposing strain gauges on said surface for measuring deflection of said surface in response to the collection of particles thereon.

27. A system for collecting, for image analysis, biological particles from a fluid medium, said system comprising tag means for dispersing in the fluid medium and comprising magnetically responsive material having a selectable magnetic state and having at least one substance immobilized upon an exterior surface with specific affinity for an epitope on said biological particles, magnetic field source means for generating within said fluid medium a magnetic field to select said magnetic state of said tag elements coupled to said biological particles, and for establishing a flow of biological particles within said fluid medium, plate means having a surface for positioning within said flow for collecting biological particles thereon, and transfer means, coupled to said plate means, for removing said surface with said collected biological particles from said fluid medium.

28. A system according to claim 27 further including means for removing said particles from said surface onto an optical element with a spatial distribution of particles substantially similar to the distribution of said biological particles collected on said surface.

29. A system according to claim 27 further comprising means for measuring a parameter responsive to the collection of particles against said surface and wherein the value of said parameter changes according to the quantity of biological particles collected thereon.

30. A system according to claim 27 wherein said magnetic field source means produces a magnetic field to hold said biological particles against said surface of said plate means as said surface is removed from said fluid medium.

31. A system according to claim 1 further including means for removing said biological particles from said surface of said plate means onto an optical element with a spatial distribution of particles substantially similar to the distribution of said particles collected on said surface.

* * * * *